United States Patent [19]

Reed et al.

[11] Patent Number: 5,512,667
[45] Date of Patent: Apr. 30, 1996

[54] TRIFUNCTIONAL INTERMEDIATES FOR PREPARING 3'-TAILED OLIGONUCLEOTIDES

[76] Inventors: Michael W. Reed, 3575 NE. 180th, Seattle, Wash. 98105; Rich B. Meyer, Jr., 15411 NE. 176th Pl., Woodinville, Wash. 98072

[21] Appl. No.: 12,896

[22] Filed: Feb. 3, 1993

Related U.S. Application Data

[63] Continuation of Ser. No. 574,348, Aug. 28, 1990, abandoned.

[51] Int. Cl.$^6$ ............................. C07H 21/04; C07F 9/06; C07F 7/04; C07D 219/08
[52] U.S. Cl. .................. 536/24.31; 536/24.3; 536/24.32; 546/106; 548/116; 552/544; 556/405
[58] Field of Search ............................... 536/25.3, 25.31, 536/25.32; 546/106; 548/116; 552/544; 556/405

[56] References Cited

U.S. PATENT DOCUMENTS

| | | | |
|---|---|---|---|
| 5,141,813 | 8/1992 | Nelson | 428/402 |
| 5,401,837 | 3/1995 | Nelson et al. | 536/25.32 |
| 5,451,463 | 9/1995 | Nelson et al. | 428/402 |

FOREIGN PATENT DOCUMENTS

| | | | |
|---|---|---|---|
| 89/02439 | 3/1989 | WIPO . | |

OTHER PUBLICATIONS

Stanfield et al. J. Org. Chem. 46: 4799, 1981.

T. Saison–Behmoaras, et al, "Short Modified Antisense Oligonucleotides Directed Against Ha–ras Point Mutation Induce Selective Cleavage of the mRNA and Inhibit T24 Cells Proliferation", the EMBO Journal Vo. 10, No. 5, pp. 1111–1118, 1991.

Frank Seela, et al, "Oligodeoxyribonucleotides Containing 1,3–Propanediol As Nucleoside Substitute", IRL Press Limited, Oxford, England, Nucleic Acids Research, vol. 15, No. 7, 1987.

Robert L. Letsinger, et al., "Cholesteryl–conjugated Oligonucleotides Synthesis: Properties, and Activity as Inhibitors of Republication of Human Immunodeficiency Virus in Cell Culture", Proc, Natl. Acad, Sci, USA, vol. 86, pp. 6553–6556, Sep. 1989, Biochemistry.

Ulysse Asseline, et al., "Nucleic Acid–Binding Molecules with High Affinity and Base Sequence Specificity: Intercalating Agents Covalently Linked to Oligodeoxynucleotides", Proc. Natl. Acad. Sci, U.S.A., vol. 81, pp. 3297–3301, Jun. 1984, Biochemistry.

Paul S. Nelson et al., "Bifunctional Oligonucleotide Probes Synthesized Using a Novel CPG Support Are Able to Detect Single Base Pair Mutations", Nucleic Acids Research, vol. 17, No. 18, 1989, pp. 7187–7194.

J. Synese, et al, Chem. Abst. 106: 213981q, p. 652, vol. 106, 1987.

Michael W. Reed, et al, "Acridine– and Cholesterol– Derivatized Solid Supports for Improved Synthesis of 3'–Modified Oligonucleotides", Bioconjugate Chemistry, No. 2, American Chemical Society, 1991, pp. 217–225.

R. T. Pon et al., "Derivatization of Controlled Pore Glass Beads for Slid Phase Oligonucleotide Synthesis", BioTechniques, 6(8): 768–775 (1988).

T. Atkinson et al., "Solid–Phase Synthesis of Oligodeoxyribonucleotides by the Phosphite–triester Method", Oligonucleotide Synthesis, A. Practical Approach, M. J. Gait, ed. IRL Press, pp. 35–81 (1984).

J. C. Francois et al., "Periodic Cleavage of Poly(dA) by Oligothymidylates Covalently Linked to the 1,10–Phenanthrioline–Copper Complex," Biochemistry 27: 2272–76 (1988).

G. B. Dreyer et al., "Sequence–Specific Cleavage of Single–Stranded DNA: Oligodeoxynucleotide–EDTA.FE(II)," Proc. Natl. Acad. Sci. U.S.A. 82: 968–72 (Feb. 1985).

C. F. Stanfield et al., "Synthesis of Protected Amino Alcohols: A Comparative Study," J. Org. Chem. 46: 4799–4800 (1981).

*Primary Examiner*—Gary L. Kunz

[57] ABSTRACT

Oligonucleotides having a low molecular weight tail molecules joined to the 3' terminus of the oligonucleotide via a linking molecule of the structure:

Z is

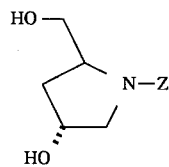

or

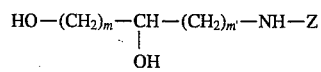

wherein

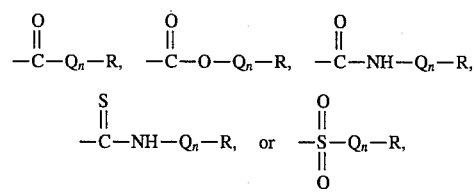

m and m' are positive integers less than 11, n is 0 or 1 and Q is a connecting group, are synthesized by selectively reacting three independent functional groups on the linking molecule, i.e., an amine, a primary hydroxyl and a secondary hydroxyl, in a stepwise manner. A tail molecule R is first connected to the amino functionality of the linking molecule. Next the linking molecule-tail molecule combination is attached to a solid state support via the secondary hydroxyl group. The oligonucleotide is systematically stepwise synthesized beginning on the primary hydroxyl group followed by release of the oligonucleotide having the low molecular weight tailed joined to its 3' terminus from the solid state support.

16 Claims, No Drawings

TRIFUNCTIONAL INTERMEDIATES FOR PREPARING 3'-TAILED OLIGONUCLEOTIDES

CROSS-REFERENCE TO RELATED APPLICATION

The present application is a continuation of application Ser. No. 07/574,348, filed on Aug. 28, 1990, now abandoned.

BACKGROUND OF THE INVENTION

This invention is directed to a method of synthesis of oligonucleotides having low molecular weight tail molecules joined to the 3'-terminus of the oligonucleotide via a linking molecule, to oligonucleotides having low molecular weight tail molecules joined to their 3'-terminus and to intermediates utilized for the synthesis of such oligonucleotides.

Oligonucleotides have various uses including acting as primers for polymerase chain reaction synthesis of DNA. Oligodeoxynucleotides (abbreviated as ODN) are conveniently synthesized on solid phase supports using phosphite-triester synthetic methods. A detailed review of such syntheses was published in Atkinson, T., Smith, M. (1984) in *Oligonucleotide Synthesis, A Practical Approach*, Gait, M. J. (ed.), IRL Press, pp. 35–81. This review gives detailed step by step conditions for the practical synthesis of oligonucleotides. Indeed, methods as outlined in this review are presently utilized in commercial oligonucleotide synthesizers available from various manufacturers.

Asseline, et al., *Proc. Natl. Acad. Sci.* 81:3297–3301 (1984), describes the synthesis of certain oligonucleotides wherein an intercalating agent was covalently linked to the oligodeoxynucleotides. The intercalating agent utilized was 2-methoxy-6-chloro-9-aminoacridine. The acridine molecule was covalently linked to an oligodeoxynucleotide via a methylene chain of from 3 to 6 carbon atoms connecting the 3'-phosphate of the oligodeoxynucleotide to the 9-amino group of the acridine. The authors of this study found that the acridine modified oligonucleotides in the presence of a complementary sequence showed strong stabilization by the intercalating agent, i.e., the acridine. These authors measured certain thermodynamic parameters and showed via these parameters that the covalent attachment of the acridine ring strongly stabilized the binding of a synthetic oligonucleotide to its complementary sequence. The melting temperature, i.e., $T_m$, of an oligonucleotide having the intercalating agent attached thereto and its complementary strand was increased compared to the melting temperature of a similar oligonucleotide not bearing the intercalating agent thereon and its complementary strand. The authors concluded that the results clearly show that the presence of the intercalating agent strongly stabilized the complex formed between an oligonucleotide and its complementary strand.

In a similar study Letsinger, et al., *Proc. Natl. Acad. Sci.* 86:6553–6556 (1989), prepared a family of oligonucleotides that had a cholesteryl group covalently joined at the 3'-terminal internucleoside phosphate linkage. Oligomers of various length were synthesized. Those bearing the cholesteryl moiety adjacent either the 3' terminus or both the 3' and the 5' terminus were compared to oligomers that were not so substituted. These compounds were tested as to their inhibitory action on HIV-1 replication. Anchoring of a single cholesteryl fragment adjacent to the 3' terminus of a 20-mer oligonucleotide significantly enhanced the antiviral activity of the oligonucleotide. Anchoring of the second cholesteryl fragment at the 5' terminus of the oligonucleotide detracted and led to a reduction of activity compared to the monocholesteryl derivatized oligomer.

The compounds of Letsinger, et al. were prepared by first manually preparing a support bound dinucleoside hydrogen phosphonate derivative. A cholesteryl group was then tethered to the internucleoside phosphorus by oxidative phosphoramidation. The oligonucleotide was elongated from the original dinucleotide on a commercial DNA synthesizer using phosphoramidite chemistry.

Controlled pore glass beads for use in commercial oligonucleotide synthesis are available from Pierce Chemical Co. and Sigma Chemical Co. As is described in Atkinson and Smith, above, the controlled pore glass beads, hereinafter alternately referred to as CPG's, are derivatized by the manufacturers with a long chain alkylamine group such that a free amino group is available at the end of the long chain alkylamine that in turn is attached to the CPG. Various amide linkages can be formed with the terminal amine of the long chain alkylamine on the CPG's for attachment of a growing oligonucleotide during synthesis of the same. An improvement of this synthesis was reported by Pon, et al., *BioTechniques* 6(8):768 (1988). In this report Pon, et al. precap a suspected contaminate side group on the long chain alkylamine CPG and introduce the use of DEC (a water soluble carbodiimide, i.e., 1-(3-dimethylaminopropyl)-3-ethylcarbodiimide) in place of the more commonly used (and toxic) linking agent DCC, i.e., dicyclohexylcarbodiimide.

Nelson, et al., *Nuc. Acid Research* 17(18):7187–7194 (1989), recently described the synthesis of an oligonucleotide incorporating a 3'-terminal substituent thereon. To prepare a 3' tailed oligonucleotide, Nelson, et al. derivatized the secondary hydroxyl of N-Fmoc-O-DMT-3-amino-1,2-propanediol by treating with succinic anhydride in the presence of DMAP (dimethylaminopyridine) and then subsequently treated with p-nitrophenol in DCC. The activated derivative was then anchored to a long chain alkylamine CPG support. The dimethoxytrityl blocking group was removed from the primary alcohol of the propanediol and a oligonucleotide was synthesized stepwise from the primary hydroxyl group while supported on the CPG support. The synthetic oligonucleotide was deprotected and cleaved from the CPG support. At this juncture in this synthesis the 3'-terminal tail substituent has yet to be coupled to the oligonucleotide. The crude oligonucleotide was biotinylated with a "Biotin-XX-NHS" ester. After biotinylation, a second purification was necessary by both Sephadex and by HPLC. No yield data was given.

The above procedure of Nelson, et al., gives an oligonucleotide with an amine functional group that may be derivatized (modified) with a "tailing reagent", then repurified. However, the derivation with the "tailing reagent" is effected only after the synthesis of the oligonucleotide is complete. By effecting the derivation on a completed oligonucleotide, precious oligonucleotide that has been systematically stepwise assembled, nucleotide by nucleotide, can be lost to incomplete reaction, side reactions and/or multiple purifications necessary after the derivation. Additionally, this synthesis did not take advantage of the above Pon, et al. improvement.

BRIEF DESCRIPTION OF THE INVENTION

The usefulness of oligonucleotides can be enhanced by including small molecular weight groups at their 3' end as, for instance, the above referred to 3'-tailed cholesterol and 3'-tailed acridine oligonucleotides of Letsinger, et al. and Asseline, et al. It is a broad object of this invention to provide an improved method of synthesis of oligonucleotides having low molecular weight tail molecules joined to the 3' terminus of the oligonucleotide. It is a further object to provide a method of synthesis of oligonucleotides having a low molecular weight molecule joined to the oligomer via a linking molecule. It is an additional object of this invention to provide for oligonucleotides derivatized about their 3' terminus with a phosphate ester and a tail molecule joined to that phosphate ester. It is a further object to provide for a linking molecule and a support system suitable for the preparation of oligonucleotides thereon. Further, it is an object to provide for a linking molecule bearing an appropriate small molecular weight molecule onto which an oligonucleotide can be constructed.

These and other objects as will become evident from the remainder of this specification are achieved in a method of synthesis of an oligonucleotide having a low molecular weight tail molecule joined to its 3' terminus via a linking molecule. The method includes selecting as the linking molecule a molecule having three independent functional groups with the chemical reactivity of each of the three functional groups being independent and distinct from the reactivity of the other two of the functional groups. The first functional group of the linking molecule is reacted with a low molecular weight tail molecule to join the tail molecule to the linking molecule. The second functional group of the linking molecule is reacted with a solid phase support to connect or anchor the linking molecule having the tail molecule joined thereto to the solid phase support. A first 3'-phosphoramidite nucleotide is then reacted with the third functional group of the linking molecule to attach the first nucleotide via its 3' terminus to the linking molecule. The attachment of the first nucleotide to the linking molecule joins the first nucleotide to the tail molecule via the linking molecule and connects or anchors the first nucleotide to the solid phase support also via the linking molecule. Further 3'-phosphoramidite nucleotides are subsequently reacted with the 5' end of a preceding nucleotide to form a synthetic oligonucleotide attached to the linking molecule at the oligonucleotide's 3' terminus. As with the first nucleotide, the attachment of the synthetic oligonucleotide via its 3' terminus to the linking molecule concurrently joins the oligonucleotide to the tail molecule and to the solid phase support. Thus the growing oligonucleotide is attached to the solid phase support during the reactions of the further nucleotides with the growing oligonucleotide. The oligonucleotide having the tail molecule joined to its 3' terminus via the linking molecule is then disconnected from the solid phase support by cleaving the connection between the second functional group of the linking molecule and the solid phase support. The oligonucleotide having the tail molecule joined to its 3' terminus via the linking molecule can then be isolated.

In a preferred embodiment of the invention the functional groups on the linking molecule include a primary alcohol, a secondary alcohol and an amine. The tail molecule is reacted with the amine to join the tail molecule to the linking molecule, the solid phase support is reacted with the secondary alcohol to connect the linking molecule having the tail molecule joined thereto to the solid phase support and the first phosphoramidite nucleotide is reacted with the primary alcohol to attach that first nucleotide to the linking molecule.

Particularly preferred as the linking molecule is (2S,4R)-4-hydroxy-2-hydroxymethylpyrrolidine (also designated as 4-hydroxy-(2S-trans)-2-pyrrolidinemethanol or trans-4-hydroxy-L-prolinol).

The tail molecule can be selected as any one of a number of molecules of interest including reporter groups, intercalating groups, lipophilic groups and cleaving groups. Suitable as a lipophilic group would be cholesterol. Suitable as a reporter group would be biotin and fluorophores including acridine, fluorescein, rhodamine, Lissamine rhodamine B, Malachite Green, erythrosin, tetramethylrhodamine, eosin, pyrene, anthracene, 4-dimethylaminonaphthalene, 2-dimethylaminonaphthalene, 7-dimethylamino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarin, isoluminol, benzophenone, dansyl, dabsyl, mansyl, sulforhodamine, 4-acetamido-4'-stilbene-2,2'-disulfonic acid disodium salt, and 4-benzamido-4'-stilbene-2,2'-disulfonic acid disodium salt. Suitable as an intercalating group would be acridine, ellipticine, methidium, ethydium, phenanthroline, 2-hydroxyethanethiolato-2,2'2"-terpyridineplatinum(II) and quinoxaline and suitable as a cleaving group would be an EDTA ligand for attaching Fe and a phenanthroline ligand for attaching Cu.

For reaction with the amine of the linking molecule, the tail molecule can be selected to include an inherent connecting group or an appendant connecting group can be attached to it via an appropriate chemical synthesis. If used, after attachment, the appendant connecting group, like an inherent connecting group, is used to link the tail molecule to the linking molecule. Whether or not an inherent or an appendant connecting group is utilized, the connecting group is such that it reacts with the linking molecule to attach the tail molecule to the linking molecule.

After attaching the tail molecule to the linking molecule via the first functional group but prior to joining the linking molecule to the solid state support, the third function group of the linking molecule can be selectively blocked. The linking molecule bearing the blocked third functional group is then attached to the solid state support via the second functional group. The third functional group is then deblocked and the first phosphoramidite nucleotide is attached to the linking molecule via the deblocked third functional group.

The objects of the invention are further achieved in a derivatized oligonucleotide having a 3'-terminal hydroxyl. A phosphate ester is located on that 3'-terminal hydroxyl and is of the structure:

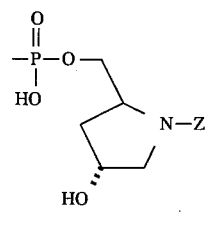

or

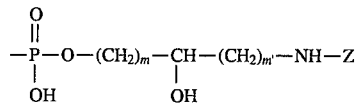

wherein

Z is

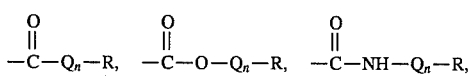

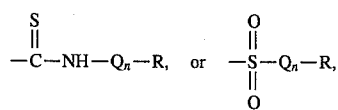

m and m' independently are positive integers less than 11, n is 0 or 1, Q is a connecting group and R is selected from the group consisting of reporter groups, intercalating groups, lipophilic groups and cleaving groups.

Of this group, particularly preferred are compounds of the structure:

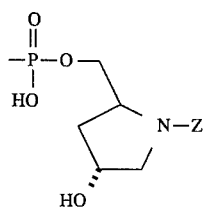

Particularly preferred 3'-tailed oligonucleotides would include an oligonucleotide having either cholesterol or acridine joined via a linking molecule to the oligomer's 3' tail. The cholesterol moiety is bonded to the linking molecule utilizing a carbamate linkage and the acridine moiety, preferably 9-ethylacridine, is joined to the oligonucleotide utilizing an amide linkage (in effect an alkylamine linkage if the ethyl group of the 9-ethylacridine is considered). Other tail groups can be joined to the linking molecule via urea, thiourea or sulfonamide linkages.

In attaching the tail molecule to the linking molecule, the connecting group Q can preferably be selected from the group consisting of alkyl, alkoxy, alkoxyalkyl, alkenyl, cycloalkyl, aryl, aryloxy, aralkyl, heterocyclic, heteroaryl, substituted aryl and substituted aralkyl.

Further objects of the invention are achieved in a compound and support for oligonucleotide synthesis comprising: a compound of the structure:

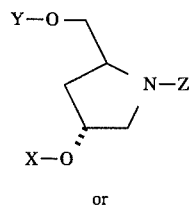

or

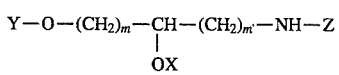

Z is
wherein

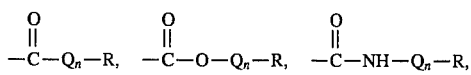

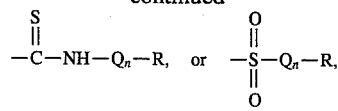

m and m' independently are positive integers less than 11, n is 0 or 1, Q is a connecting group, R is selected from the group consisting of reporter groups, intercalating groups, lipophilic groups and cleaving groups, Y is H or dimethoxy trityl and X is solid phase support. Useful supports include controlled pore glass supports derivatized with long chained alkylamines.

Of this group, particularly preferred are compounds of the structure:

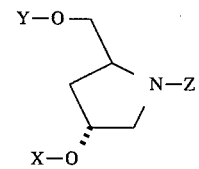

The objects of the invention are further achieved in a compound of the structure:

Z is

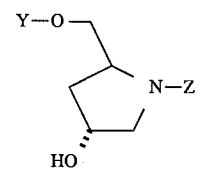

or

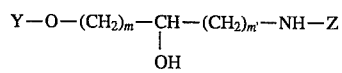

wherein

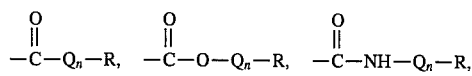

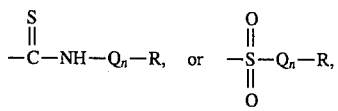

m and m' independently are positive integers less than 11, n is 0 or 1, Q is a connecting group, R is selected from the group consisting of reporter groups, intercalating groups, lipophilic groups and cleaving groups and Y is H or dimethoxy trityl.

Of this group, particularly preferred are compounds of the structure:

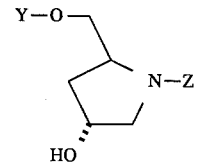

In each of the above structures m and m' are positive integers less than 11, that is m and m' independently are 1, 2, 3, 4, 5, 6, 7, 8, 9 or 10. Particularly preferred are compounds wherein m and m' are 6 or less that is m and m' independently are 1, 2, 3, 4, 5 or 6.

DETAILED DESCRIPTION OF THE INVENTION

We have found that an oligonucleotide can be synthesized having a low molecular tail molecule joined to the 3' terminus of the oligonucleotide by use of a linking molecule. The linking molecule is selected to have three chemically distinct functional groups on it. When such a linking molecule is utilized, a low molecular weight tail molecule is first joined to the linking molecule. The linking molecule with its low molecular weight tail molecule is then joined or anchored to a solid phase support. The oligonucleotide is then synthesized. During its synthesis it is anchored on the linking molecule which in turn is anchored to the solid state support system. The oligonucleotide is synthesized using standard phosphoramidite chemistry, either manually or on a DNA synthesizer. When the synthesis of the oligonucleotide is completed, the linking molecule having the synthesized oligonucleotide and a low molecular weight tail molecule joined to it, is cleaved from the solid state support. This frees the oligonucleotide from the support system. The oligonucleotide now has the small molecular weight tail molecule joined to its 3' terminus via the linking molecule.

Using the above preparative steps oligonucleotides having low molecular weight tail molecules joined to their 3' terminus need only be subjected to a single purification step. Thus, compared to the prior art, oligonucleotides having molecules of interest joined to their 3' terminus are prepared in a facile and expeditious manner.

The linking molecule having an appropriate low molecular weight molecule of interest attached to it can be synthesized independent of the oligonucleotide synthesis. Once a linking molecule having a tail molecule of interest linked thereto is prepared by reacting the tail molecule with the first functional group of the linking molecule, the combination of the linking molecule and the tail molecule can be considered as a reagent suitable for use in a DNA synthesizer for preparation of numerous different oligonucleotides each of which have the low molecular weight molecule attached to their 3' terminus. This allows for large scale synthesis and storage, if desired, of the linking molecule-tail molecule combination. Additionally other combinations of the linking molecule with various other tail molecules also can be prepared in the same manner. These can then be used by non-organic chemical personnel for oligonucleotides synthesis using DNA synthesizers. Thus personnel not skilled in synthetic organic chemical disciplines can easily use aliquots of the linking molecule-tail molecule combinations as a first reagent in such automatic DNA synthesizers for synthesis of oligonucleotides having selected low molecular weight tail molecules joined to their 3' terminus.

Further, multiple oligonucleotides that may have a common sequence for a number of nucleotide and then a divergent sequence for the remainder of the oligonucleotides but all of which have the same 3'-tail molecule of interest attached via the linking molecule, can be prepared by simply subdividing into aliquots the solid state support having a partially formed "common" oligonucleotide and its attaching linking molecule and tail molecule of interest. The synthesis of the divergent segments of the oligonucleotides is then completing by loading an individual aliquot of the solid state support having the common segment of the oligonucleotide on the DNA synthesizer and completing the desired sequence of nucleotides.

The compound (2S,4R)-4-hydroxy-2-hydroxymethylpyrrolidine, compound 2 of Scheme I, (also identifiable as 4-hydroxy-(2S-trans)-2-pyrrolidinemethanol or trans-4-hydroxy-L-prolinol) serves as a particularly useful linking molecule for attaching molecules of interest to the 3' terminus of an oligonucleotide. This compound is readily prepared from commercially available N-CBZ-L-hydroxyproline (Sigma Chemical Company). Reduction of the N-CBZ-L-hydroxyproline utilizing a procedure similar to that described by Stanfied, et al., *J. Org. Chem.* 46:4799 (1981) is readily accomplished in a borane-THF complex (Aldrich Chemical Co.). This reduction proceeds with retention of the optical purity of compound 2. For compound 2, after reduction of the CBZ protected hydroxyproline to the corresponding 2-hydroxymethyl pyrrolidine, the CBZ protecting group is easily removed utilizing a palladium on charcoal reduction under a balloon of hydrogen. This reaction proceeds smoothly giving a quantitative yield of compound 2.

Compound 2 includes a primary hydroxyl group that is utilized as the foundation on which an oligonucleotide is synthesized. Further compound 2 includes a secondary alcohol group that is utilized for attachment to a solid state support and a secondary amine that is utilized for attaching a tail molecule of interest. After synthesis of the oligonucleotide is completed, the tail molecule of interest remains attached to the oligonucleotide via the linking molecule. After cleavage from the solid state support of the completed oligonucleotide including the molecule of interest joined thereto via the linking molecule, the secondary hydroxyl group of the linking molecule is essentially held rigid in space and is removed from the vicinity of the phosphate linkage that attaches the linking molecule to the first nucleoside. This results in increased stability of the bond between the linking molecule and the oligonucleotide's 3' terminal phosphate group.

Further, since compound 2 is a single optical isomer and is not a mixture of stereoisomers, the bond between the 3' terminus of the oligonucleotide and this linking molecule also yields a single isomer and not a mixture of stereoisomers that might affect the physical properties. This may be particularly importance when attaching intercalating groups to the 3' terminus end of an oligonucleotide because of a potential requirement for precise geometry for optimum binding of the intercalating agent with the double stranded complex of the oligonucleotide and its complementary DNA segment.

Other linking molecules are compounds of the structure:

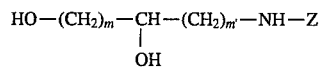

where m and m' are positive integers from 1 to 10, inclusive. These linking molecules also have an amino, a primary hydroxyl and a secondary hydroxyl functional group included in their structure. Two particularly useful linking molecules of this class are 3-amino-1,2-propanediol and 4-amino-1,3-butanediol.

Attachment of the tail compound of interest to the linking molecule is done completely independent of any oligonucleotide synthesis as described above. A low molecular weight tail molecule of interest is attached to the linking molecule utilizing organic chemistry techniques and reactions. The secondary amino group of linking molecule is utilized to link the low molecular weight tail molecule of interest to the linking molecule, e.g. compound 2, via any one of a number of suitable connections or linkage, as for instance an amide linkage, a carbamate linkage, an urea linkage, a thiourea linkage, or a sulfonamide linkage. Given this disclosure other suitable reactions between the secondary amine of linking molecule, e.g. compound 2, and appropriate connecting or linking groups on compounds of interest also will be suggested to the art skilled.

For the purposes of clarity of this specification and the claims attached hereto, to avoid confusion between the above referenced "linking molecule" and any further "linking group" that might be used to attach a tail molecule to this linking molecule, the terminology "connecting group" is utilized to indicated these connecting or linking groups. Irrespective of the name given to these groups, they link, connect or bond a tail molecule to the linking molecule.

After the molecule of interest, which eventually will be at the 3' tail of the oligonucleotide, is connected to the linking molecule, the primary hydroxyl group on the linking molecule is appropriately protected, as for instance with a dimethoxytrityl group. This is conveniently accomplished utilizing dimethoxytritylchloride (DMTrCl) in pyridine in the presence of 4-dimethylaminopyridine (DMAP). This selectively protects the primary alcohol group of the linking molecule. The secondary alcohol of the linking molecule is then converted to a succinate ester utilizing succinic anhydride. The succinic ester of the linking molecule bearing the low molecular weight compound of interest thereon can be coupled to a controlled pore glass support utilizing either the older p-nitrophenol-DCC method of Atkinson, et al., above, or preferably using the facilitated DEC method of Pon, et al., above. Insofar as DEC is less toxic than DCC, is water soluble and eliminates the necessity of treating the succinic ester with p-nitrophenol, it is the presently preferred method.

The dimethoxytrityl protected linking molecule bearing a low molecular weight compound of interest attached thereto is then coupled or anchored to a controlled pore glass support having a long chain alkylamine group attached thereto in the normal manner. Controlled pore glass supports derivatized with long chain alkylamines are available from Pierce Chemical or from Sigma Chemical. These are preactivated utilizing the procedure of Pon, et al., above, with dichloroacetic acid and then reacted in pyridine utilizing DEC as the coupling reagent with the dimethoxytrityl protected linking molecule having the molecule of interest attached thereto. After attachment of the linking molecule to the solid state support, excess long chain alkylamino groups on the support are capped by acetylating the same with acetic anhydride.

The dimethoxytrityl group is removed from the primary alcohol of the linking molecule by treating with 3% dichloroacetic acid in dichloromethane. The resulting controlled pore glass support, having the low molecular weight tail molecule attached thereto via the linking molecule (and with the primary hydroxyl group of the linking molecule now deblocked), is now ready for synthesis of the oligonucleotide thereon. It is recognized that the solid state support loaded with the linking molecule and molecule of interest can also be prepared in bulk and then subdivided for the synthesis of multiple oligonucleotides or even stored for later use. In any event oligonucleotide synthesis is initiated from the primary hydroxyl group of the linking molecule using phosphoramidite chemistry on a DNA synthesizer, as for instance a Milligen DNA synthesizer, in a normal manner.

Once synthesis of the oligonucleotide is complete, the oligonucleotide is deprotected in the standard manner for oligonucleotides synthesized on automated DNA synthesizers. The oligonucleotide with the low molecular tail molecule joined to its 3' terminus via the linking molecule is then cleaved from the solid state support also in the normal manner for automated DNA synthesis utilizing concentrated ammonia at room temperature in the normal manner.

Only a single purification step is necessary to purify the oligonucleotide having the low molecular weight tail molecule joined to its 3' terminus via the linking molecule. This can conveniently be done utilizing reverse phase HPLC chromatography.

The low molecular weight tail molecule to be joined to the 3' terminus of the oligonucleotide can be any one of a number of molecules of biological interest. Included in this group would be reporter groups, intercalating groups, lipophilic groups and cleaving groups. Particularly preferred at this time for the lipophilic group is cholesterol. Particularly preferred at this time for reporter group are biotin and the fluorophores including acridine, fluorescein, rhodamine, Lissamine rhodamine B, Malachite Green, erythrosin, tetramethylrhodamine, eosin, pyrene, anthracene, 4-dimethylaminonaphthalene, 2-dimethylaminonaphthalene, 7-dimethylamino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarin, isoluminol, benzophenone, dansyl, dabsyl, mansyl, sulfo rhodamine, 4-acetamido-4'-stilbene-2, 2'-disulfonic acid disodium salt, 4-benzamido-4'-stilbene-2, 2'-disulfonic acid disodium salt. Particularly preferred at this time for the intercalating group are acridine, ellipticine, methidium, ethydium, phenanthroline, 2-hydroxy-ethanethiolato-2,2',2"-terpyridine-platinum(II) and quinoxaline. Particularly preferred at this time for the cleaving group would be an EDTA ligand for attaching iron and a phenanthroline ligand for attaching copper.

For those tail molecules that do not contain an inherent connecting group for attaching the tail molecule to the amino group of the linking molecule, the tail molecule is reacted with an appropriate reagent to attach an appendant connecting group thereon that is capable of reacting with the amine substituent of the linking molecule. Thus, irrespective of whether or not the tail molecule has an inherent connecting group that is capable of reacting with the amine of the linking molecule, or whether an appendant connecting group must be attached thereto for reacting with the amino group of the linking molecule, the tail molecule is reacted with the amino group of the linking molecule to attach the tail molecule to the linking molecule.

For attaching a tail molecule R via linking molecules

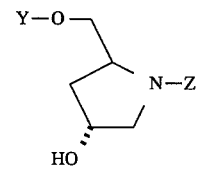

or

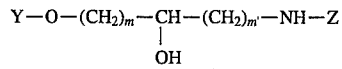

of the invention,

Z is selected from one of the structures:

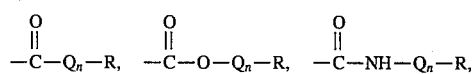

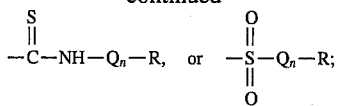, or 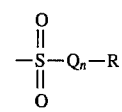

m and m' independently are selected to be positive integers less than 11, n is selected as 0 or 1, and Q is a connecting group. The tail molecule R is selected from the group consisting of reporter groups, intercalating groups, lipophilic groups and cleaving groups and Y is H or dimethoxytrityl.

As for instance cholesterol chloroformate is reacted with the linking molecule to attach the cholesterol group to the linking molecule via a carbamate connecting group. In a further example 9-acridinepropionic acid is reacted with the linking molecule yielding 9-ethylacridine attached linking molecule via an amide linkage.

If the above referenced cholesterol chloroformate is used as the precursor of the tail molecule, n is 0 thus Q is absent and Z therefore is:

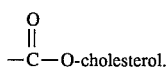

If the above referenced 9-acridinepropionic acid is used as the precursor of the tail molecule, n is 1 thus Q is present and is an alkyl moiety, i.e., ethyl. In this instance Z is:

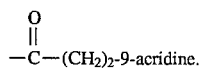

When n is 1 and Q is present, suitable for use as the connecting group Q are alkyl, alkoxy, alkoxyalkyl, alkenyl, cycloalkyl, aryl, aryloxy, aralkyl, heterocyclic, heteroaryl, substituted aryl and substituted aralkyl groups.

Useful as precursor molecules for preparations of compounds the above formula wherein Z is a carbamate of the structure:

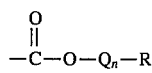

are chloroformates. Useful as precursor molecules for preparation of compounds of the above formula wherein Z is a urea of the structure:

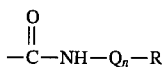

are isocyanates. Useful as precursor molecules for preparation of compounds of the above formula wherein Z is a thiourea of the structure:

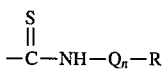

are isothiocyanates. Useful as precursor molecules for preparation of compounds of the above formula wherein Z is a sulfonamide of the structure:

are sulfonyl halides.

Various sulfonyl halide precursors tail molecules are available from Molecular Probes, Inc., Eugene, Oreg. Such sulfonyl halides are aromatic sulfonyl halides wherein the sulfonyl halide moiety is present as an inherent connecting moiety on one of the rings of a tail molecule of interest, as for instance a rhodamine, a naphthalene, a pyrene, or an anthracene ring. In such instance in the above formula n is 0 and the connecting group Q is therefore absent. Generally the halide ion is chlorine or fluorine however bromine and iodine might also be useful.

Useful sulfonyl halides include sulforhodamine sold by Molecular Probes, Inc. under the tradename "Texas Red." Further would be Lissamine rhodamine B sulfonyl chloride, Lissamine rhodamine B sulfonyl fluoride, 5-dimethylaminonaphthalene-1-sulfonyl chloride (dansyl chloride), 2-dimethylaminonaphthalene-5-sulfonyl chloride, 2-dimethylaminoaphthalene-6-sulfonyl chloride, 6-(N-methylanilino)naphthalene-2-sulfonyl chloride (mansyl chloride), 1-pyrenesulfonyl chloride, 2-anthracenesulfonyl chloride, 5-dimethylaminonaphthalene-1-sulfonyl fluoride (dansyl fluoride), and 4-dimethylaminoazobenzene-4'-sulfonyl chloride (dabsyl chloride).

Various isothiocyanates precursor tail molecules are useful for preparing thiourea linkages between the tail molecule and the linking molecule. As with the above sulfonyl halides, generally the isothiocyanates is present as an inherent connecting moiety on an aromatic ring of the tail molecule, and as such, in the above formula, n is also 0 and therefore Q would be absent. Such isothiocyanates are also available from Molecular Probes, Inc.

Suitable isothiocyanates for reacting with the linking molecule include fluorescein-5-isothiocyanate, fluorescein-6- isothiocyanate, tetramethylrhodamine-5-(and-6)-isothiocyanate, Rhodamine X isothiocyanate, Malachite Green isothiocyanate, eosin-5-isothiocyanate, erythrosin-5-isothiocyanate, 7-diethylamino-3-(4'-isothiocyanatophenyl)-4-methylcoumarin, p-(5-dimethylaminonaphthalene-1-sulfonyl)aminophenylisothiocyanate, N-(4-(6-dimethylamino-2-benzofuranyl)phenylisothiocyanate hydrochloride, 1-pyreneisothiocyanate, 2-anthraceneisothiocyanate, 4-dimethylaminonaphthyl-1-isothiocyanate, 9-acridine isothiocyanate, 4-isoluminol isothiocyanate, 4-dimethylaminophenylazophenyl-4'-isothiocyanate, benzophenone-4-isothiocyanate, 4,4'-diisothiocyanatostilbene-2,2'-disulfonic acid disodium salt, 4,4'-diisothiocyanatodihydrostilbene-2,2'-disulfonic acid, disodium salt, 4-acetamido-4'-isothiocyanatostilbene-2,2'-disulfonic acid disodium salt, and 4-benzamido-4'-isothiocyanatostilbene-2,2'-disulfonic acid disodium salt.

Other useful precursors molecules for the tail molecule including examples wherein n is 1 and thus a connecting group Q is present include 5-(and 6-)carboxyfluorescein diacetate succinimidyl ester, 7-dimethylaminocoumarin-4-acetic acid, 7- amino- 4-methylcoumarin-3-acetic acid, 7-diethylaminocoumarin-3-carboxylic acid, 7-hydroxycoumarin-4-acetic acid, 7-hydroxy-4-methylcoumarin-3-acetic acid, 7-hydroxycoumarin-3-carboxylic acid, 7-methoxycoumarin-3-carboxylic acid, 7-carboxymethoxy-4-methylcoumarin, 7-acetoxycoumarin-3-carboxylic acid, acridone-2-acetic acid, acridone-10-acetic acid, 9-anthracenepropionic acid, 1-pyrenebutanoic acid (pyrenebutyric acid) and N-(5- dimethylaminonaphthalene-1-sulfonyl)glycine (dansyl glycine).

EDTA.Fe(II) has been used as a cleaving group in conjunction with a oligonucleotide. The EDTA molecule was attached to the base of a uridine nucleoside. A carboxyl terminated chain was extended from the uracil moiety and the EDTA attached to it. While this approach yields a nucleoside having EDTA attached to it, any oligonucleotide that incorporated such a nucleoside might suffer from the EDTA molecule interfering with initial base paring between the oligomer and its complementary DNA stand since the EDTA is on the base. By use of the linking molecule of this invention, an EDTA moiety can be extended from the linking molecule away from the nucleotide's base and thus in a more non-interfering position for initial base paring with a complementary stand of DNA.

Reaction of the linking molecule with an alkyl isocyanate as, for instance ethyl isocyanatoacetate, followed by treatment with ethylenediamine and EDTA-triethylester-N-hydroxysuccinimide ester would serve to attach the EDTA moiety to the linking molecule via amide linkages. In this instance an appendant connecting group is utilized to form the attaching bonds of the EDTA cleaving group with the linking molecule. Cleavage reaction conditions are initiated in aqueous solution by adding Fe(II) and an appropriate oxidant such as dithiothreitol in a manner as is set forth in Dreyer, et al., *Proc. Natl. Acad. Sci.* 82:968–972 (1985).

In attaching a further cleaving group, phenanthroline-Cu(I) complex, 1,10-phenanthroline can be aminated at the 5 or 6 position. The amine can then be succinylated. The resulting terminal carboxylate would then be activated, as for instance by converting to a N-hydroxysuccinimide ester, for reaction with the amine of the linking molecule or with a further appendant connecting group that in turn is attached to the linking molecule. Cleavage with this reagent is initiated by the addition of cupric sulfate and mercaptopropionic acid in a manner similar to Francois, et al., *Biochemistry* 27:2272–2276 (1988).

In a like manner the secondary amino substituent of ellipticine might be directly succinylated with succinic anhydride in pyridine and then activated to the N-hydroxy succinimide ester (an NHS ester) with DCC in THF for attachment to the linking molecule. Quinoxaline requires amination of its ring, in a manner as per phenanthroline, prior to succinylation and activation.

Biotin having a long chain spacer is commercially available as a succinimidyl ester also from Molecular Probes, Inc. This product, 6-(6-(biotinoylamino)hexanoylamino)-hexanoic acid succinimidyl ester, is also referenced as biotin-XX succinimidyl ester. In a manner equivalent to the above phenanthroline succinimidyl ester it is reacted with the amino group of the linking molecule to join the biotin tail to the linking molecule. In a manner similar to Dervan, et al., *J. Am. Chem. Soc.* 100:1968 (1978), p-carboxymethidium can be prepared for coupling to the linking molecule via its carboxylate group. In a like manner ethydium might also be prepared.

The following illustrative examples correlate to the reaction sequences of Schemes I, II and III. In Schemes I and III the identifier "chol" indicates a cholesteryl moiety.

EXAMPLE I (2S,4R)-N-Benzyloxycarbonyl-4-hydroxy-2-hydroxymethylpyrrolidine (1)

To an ice cold solution of 4.76 g (18 mmoles) of CBZ hydroxyproline (Sigma Chemical Co.) in 20 mL of dry THF was added 45 mL of a 1M solution borane-THF complex in THF (Aldrich). After stirring under argon for 15 minutes at 0°–5° C., and 4.5 h at room temperature, the mixture was quenched with 50 mL of methanol. After 30 min, the solution was concentrated. The residual colorless syrup was purified by flash chromatography (3.5×23 cm silica) using a gradient of methanol in methylene chloride. The product eluted with 10% methanol. The fractions containing pure product were stripped of solvent to give 2.18 g (46% yield) of (1) as a colorless syrup.

TLC (95:5/methylene chloride:methanol), $R_f$=0.16. IR (neat) 3600–3100 (br), 2940, 1680, 1420 and 1355 $cm^{-1}$. $^1$H NMR (CDCl$_3$) 7.36 (s,5H), 5.17 (s, 2H), 4.50 (m, 2H), 3.67 (m,4H), 2.09 (m, 3H). Anal. Calcd for $C_{13}H_{17}NO_4 \cdot 0.3H_2O$: C, 60.83; H, 6.91; N, 5.46. Found: C, 60.85; H, 6.88; N, 5.36.

EXAMPLE II (2S,4R) -4-Hydroxy-2-hydroxymethylpyrrolidine (2)

A solution of 1.92 g (7.6 mmoles) of CBZ hydroxyprolinol (1) in 50 mL of methanol was stirred with 320 mg of 10% Pd on carbon under a balloon of hydrogen. After 16 h no starting material remained as evidenced by TLC (9:1/methylene chloride:methanol). The mixture was filtered through Celite (washed with methanol) and the filtrate was concentrated to give the desired product (2) as an amber syrup in quantitative yield. The syrup was dissolved in ethanol to give 15.2 mL of a 0.5M stock solution.

IR (neat) 3600–3100 (br), 2920, 1530 and 1410 $cm^{-1}$. $^1$H NMR (D2O) 4.40 (m, 1H), 3.60 (m, 3H), 3.02 (d of d, 1H, J=12.4, 4.8 Hz), 2.77 (d of t, 1H, J=12.4, 1.8 Hz), 1.84 (m, 1H), 1.60 (m,1HO).

EXAMPLE III (2S,4R)-N-Cholesteryloxycarbonyl-4-hydroxy-2-hydroxymethyl pyrrolidine (3)

To 7.6 mL (3.8 mmoles) of a 0.5M stock solution of hydroxyprolinol (2) in ethanol was added a solution of 1.48 g (3.3 mmoles) of cholesterol chloroformate in 8 mL of methylene chloride. The solution was stirred at room temperature for 1.5 h. The cloudy solution was poured into 100 mL of ice water and the heterogeneous mixture was extracted with 3×150 mL of hot ethyl acetate. The combined organics were washed with brine, dried over magnesium sulfate and concentrated. The solid residue was purified by flash chromatography (4×15 cm silica) using a gradient of methanol in 1:1/hexanes:ethyl acetate. The product eluted with 10% methanol. The fractions containing pure product were stripped of solvent to give 1.42 g (81% yield) of (3) as a white solid.

TLC (95:5/methylene chloride:methanol), $R_f$=0.10. Product stained black upon spraying with 10% sulfuric acid in methanol and heating. Anal. Calcd for $C_{33}H_{55}NO_4$:C, 74.81; H, 10.46; N, 2.64. Found: C, 74.74; H, 10.33; N, 2.50.

EXAMPLE IV (2S,4R)-N-cholesteryloxycarbonyl-4-hydroxy-2-dimethoxytrityloxymethylpyrrolidine (4)

To a stirred solution of 1.42 g (2.68 mmoles) of the diol (3) in 27 mL of dry pyridine was added 0.524 mL of triethylamine, 16.5 mg of 4-dimethylaminopyridine, and 1.10 g (3.23 mmoles) of dimethoxytrityl chloride. After stirring under argon for 4.5 h, the mixture was stripped of solvent. Residual pyridine was removed by co-evaporation with toluene. The residue was partitioned between 100 mL of ether and 40 mL of water. The aqueous layer was extracted with 80 mL of ether and the combined organic layers were washed with brine, dried over sodium sulfate, and concentrated. The residue was purified by flash chromatography (4.5×20 cm silica) using a gradient of ethyl acetate in hexanes. The product eluted just after a yellow impurity with 2:1/hexanes:ethyl acetate. The fractions containing pure product were stripped of solvents to give 1.33 g (60% yield) of (4) as a pale yellow solid foam.

TLC (95:5/methylene chloride:methanol), $R_f$=0.49. Product stained orange upon spraying with 10% sulfuric acid in methanol. $^1$H NMR (CDCl$_3$) 7.26 (m, 9H), 6.81 (d, 4H, J=8.8 Hz), 5.30 (m, 1H), 4.50 (m, 2H), 4.15 (m, 1 H), 3.78 (s, 6H), 3.7–3.0 (m, 4H), 2.4–0.6 (m, 46H). Anal. Calcd for $C_{54}H_{73}NO_6$: C, 77.94; H, 8.84; N, 1.68. Found: C, 77.26; H, 8.82; N, 1.56.

EXAMPLE V (2S,4R)-N-cholesteryloxycarbonyl-4-succinyloxy-2-dimethoxy trityloxymethylpyrrolidinone (5)

To a stirred solution of 1.22 g (1.47 mmoles) of the alcohol (4) in 12 mL of dry pyridine was added 443 mg (4.43 mmoles) of succinic anhydride and 89 mg (0.73 mmoles) of dimethylaminopyridine. The mixture was stirred under argon for 26 h and stripped of solvent. Residual pyridine was removed by co-evaporation with toluene. The residue was dissolved in 40 mL of chloroform, washed with brine, dried over sodium sulfate and concentrated to give quantitative yield of the product (5) as a beige solid foam.

TLC (95:5/methylene chloride:methanol), $R_f$=0.32. Product stained orange upon spraying with 10% sulfuric acid in methanol.

EXAMPLE VI

Cholesterol-CPG support (6)

The succinylated cholesterol derivative (5) was immobilized to long chain alkyl amine-controlled pore glass support (LCAA-CPG, Sigma) using a published procedure, Pon, R. T., Usman, N., and Ogilvie, K. K., Biotechniques 6:768 (1988). LCAA-CPG (5.0 g) was stirred for 3 h with 100 mL of 3% dichloroacetic acid in methylene chloride. The CPG was filtered on a 30 mL sintered glass funnel and washed with 150 mL of chloroform and 150 mL of ether. The solid was dried under vacuum and combined in a 250 mL round bottom flask with 50 mL of dry pyridine, 932 mg (1 mmole) of the succinylated cholesterol derivative (5), 0.4 mL of triethylamine, 1.92 g (10 mmoles) of 1-ethyl-3-(3-dimethylaminopropyl)-carbodiimide, and 60 mg of 4-dimethylaminopyridine. The mixture was swirled on an orbital mixer at 100 rpm for 38 h. The CPG was filtered on a 30 mL sintered glass funnel and washed with 50 mL pyridine, 100 mL of methanol, 50 mL of chloroform and 50 mL of ether, then dried under vacuum. Residual amine groups on the CPG were capped by swirling the support in 15 mL of dry pyridine and 2.0 mL of acetic anhydride. After 2 h, the CPG was filtered and washed as described above and dried under vacuum to give 5.0 g of the product (6). This material was analyzed for dimethoxytrityl content according to the published procedure (Atkinson, T.; Smith, M. (1984) in *Oligonucleotide Synthesis, a Practical Approach*, Gait, M. J. (ed.), IRL Press, p 48) and found to have a loading of 17.6 micromoles/gram of CPG support.

EXAMPLE VII

Synthesis of a 3' cholesterol tailed oligonucleotide from cholesterol-CPG

A quantity of cholesterol-CPG corresponding to 1 micromole of dimethoxytrityl content was packed into an empty column, e.g., an Applied Biosystems Inc. or Cruachem column. An oligonucleotide with the base sequence CTC-CATGTTCGTCACA was prepared on a Milligen DNA synthesizer using standard phosphoramidite chemistry. The 5'-DMTr protecting group was left on. The oligonucleotide was cleaved from the CPG and deprotected by treatment with 2 mL of conc. ammonia at room temperature for 3 days. The supernatant was injected directly on a PRP-1 reverse phase HPLC column (elution with a gradient of 20% acetonitrile to 100% acetonitrile in pH 7.5 triethylammonium acetate). The product was collected in one fraction and lyophilized to give the 5'-DMTr protected product. The DMTr group was removed by treatment with 80% acetic acid (16 h at room temperature) and repurified by HPLC. The collected product was analyzed by UV at 260 nm and found to contain 0.54 mg of product. In an alternate iteration of this procedure, the DMTr group was removed while on the synthesizer with 3% DCA to give an increased yield of the oligonucleotide.

EXAMPLE VIII (2S,4R)-N-(9-acridinepropanamidyl)-4-hydroxy-2-hydroxymethylpyrrolidine (7)

To a stirred slurry of 125.5 mg (0.5 mmoles) of 9-acridinepropionic acid (Jensen, H., and Howland, L. J., *Am. Chem. Soc.* 48:1926 (1989)) and 0.104 mL (0.6 mmoles) of ethyldiisopropylamine in 1.5 mL of methylene chloride was added 0.6 mmoles of 2-fluoro-1-methylpyridinium tosylate (FMPT). After 1.5 h at room temperature, the cloudy brown solution was added to a stirred solution of 0.5 mmoles (1.5 L) of hydroxy prolinol (2) in ethanol in an ice-salt bath. After stirring for 1 h at room temperature, the mixture was quenched with 10 mL of methanol and concentrated. The residue was purified by flash chromatography (1.5×24 cm silica) using a gradient of methanol in methylene chloride. The fractions that contained pure product were stripped of solvent to give 112 mg (64% yield) of (7) as a yellow solid foam. TLC (90:10/methylene chloride:methanol), $R_f$=0.50. Product appeared as a yellow spot with blue fluorescence.

IR (KBr) 3400 (br), 1620, 1440, 1070 cm$^{-1}$. $^1$H NMR (CDCl$_3$) 8.30 (d, 4H, J=9.4 Hz), 7.82 (t, 2H, J=6.6 Hz), 7.62 (m, 2H), 4.31 (m, 2H), 4.05 (t, 2H, J=8.2 Hz), 3.70 (m, 1H), 3.50 (m, 2H), 3.22 (d, 2H, J=1.4 Hz), 2.78 (m, 2H), 2.03 (m, 1H), 1.64 (m, 1H). Anal. Calcd for $C_{21}H_{22}N_2O_3 \cdot 0.5H_2O$: C, 70.18; H, 6.45; N, 7.79. Found: C, 70.41; H, 6.45; N, 7.68.

EXAMPLE IX (2S,4R)-N-(9-acridinepropanamidyl)-4-hydroxy-2-dimethoxy-trityloxymethylpyrrolidine (8)

To a stirred solution of 100 mg (0.285 mmoles) of the diol (7) in 2.5 mL of pyridine was added 6.4 mg of 4-dimethylaminopyridine, 0.13 mL of triethylamine and 154 mg of dimethoxytrityl chloride. After stirring for 16 h under argon, the mixture was stripped of solvent. Residual pyridine was removed by co-evaporation with methylene chloride. The residue was dissolved in 5 mL of methylene chloride and washed with 2×3 mL of water and 3 mL of brine, dried over sodium sulfate and stripped of solvent. The residue was purified by flash chromatography (1.5×20 cm silica) using a gradient of methanol in 1:1/ hexanes: ethyl acetate. The fractions containing pure product were combined and stripped of solvent to give 123 mg (66% yield) of (8) as a yellow solid foam. TLC (45:45:10/ hexanes:ethyl acetate:methanol), $R_f$=0.26. Product appeared as a yellow spot with blue fluorescence that stained orange upon spraying with 10% sulfuric acid in methanol.

IR (KBr) 3400 (br), 1620, 1440, 1070 cm$^{-1}$. $^1$H NMR (CDCl$_3$) 8.17 (m, 4H), 7.75 (t, 2H, J=7.0 Hz), 7.57–7.09 (m, 9H), 6.82 (d, 2H, J=8.8 Hz), 6.66 (m, 2H), 4.56 (m, 2H), 3.65–2.90 (m, 2H), 2.69 (m, 2H), 2.15 (m, 1H), 1.95 (m, 1H). Anal. Calcd for $C_{42}H_{40}N_2O_5 \cdot 0.5H_2O$: C, 76.23; H, 6.24; N, 4.23. Found: C, 76.53; H, 6.67; N, 3.80.

EXAMPLE X (2S,4R)-N-(9-acridinepropanamidyl)-4-succinyloxy-2-dimethoxy-trityloxymethylpyrrolidine (9)

To a stirred solution of 120 mg (0,184 mmoles) of the alcohol (8) in 1.5 mL of dry pyridine was added 55.5 mg (0.55 mmoles) of succinic anhydride and 11.2 mg of 4-dimethylaminopyridine. The mixture was stirred under argon for 40 h and stripped of solvent. Residual pyridine was removed by co-evaporation with toluene. The residue was dissolved in 3 mL of chloroform, washed with brine, dried over sodium sulfate and concentrated to give 128 mg (93% yield) of the product (9) as a yellow solid foam.

TLC (95:5/methylene chloride:methanol), $R_f$=0.13. Product appeared as a yellow spot with blue fluorescence that stained orange upon spraying with 10% sulfuric acid in methanol.

EXAMPLE XI

Acridine-CPG support (10)

The succinylated acridine derivative (9) was immobilized to a long chain alkyl amine-controlled pore glass support using the procedure described above for the cholesterol-CPG support (6). Acid washed LCAA-CPG (0.85 g) was combined in a round bottom flask with 8.5 mL of dry pyridine, 128 mg (0.170 mmoles) of the succinylated acridine derivative (9), 0.068 mL of triethylamine, 325 mg (1.7 mmoles) of 1-ethyl- 3-(3-dimethylaminopropyl)-carbodiimide, and 10.2 mg of 4-dimethylaminopyridine. The mixture was stirred under argon for 19 h. The CPG was filtered off and washed with pyridine, methanol, chloroform and ether, then dried under vacuum. Residual amine groups on the CPG were capped by stirring the support in 2.5 mL of dry pyridine and 0.34 mL of acetic anhydride. After 2 h, the CPG was filtered and washed as described above and dried under vacuum to give 0.85 g of the product (10). This material was analyzed for dimethoxytrityl content found to have a loading of 18.5 micromoles/gram of CPG support.

EXAMPLE XII

Synthesis of a 3' acridine tailed oligonucleotide from acridine-CPG

A quantity of acridine-CPG corresponding to 1 micromole of dimethoxytrityl content was packed into an oligonucleotide synthesis column. An oligonucleotide with the base sequence 5'-CTCTCCATCTTCGTCACA was prepared on a Milligen DNA synthesizer using standard phosphoramidite chemistry. The 5'-DMTr protecting group was removed on the synthesizer. The oligonucleotide was cleaved from the CPG and deprotected by treatment with 2 mL of conc. ammonia at 40° C. for 24 h. The supernatant was injected directly on a PRP-1 reverse phase HPLC column (elution with a gradient of 20% acetonitrile to 100% acetonitrile in pH 7.5 triethylammonium acetate). The product was collected in one fraction and lyophilized to give 1.99 mg (determined by UV at 260nm) of the fluorescent oligonucleotide product as a pale yellow solid.

EXAMPLE XIII

4-N-Benzyloxycarbonyl-3-hydroxybutyric acid (11)

5.0 g (42.0 mmoles) of 4-amino-3-hydroxybutyric acid (Sigma Chemical Co.) was dissolved in a solution of 3.7 g of sodium hydroxide in 35 mL of water. The solution was cooled in ice and 7.88 g (46.2 mmoles) of CBZ chloride was added dropwise over 20 min. The mixture was stirred in ice for 2 h, then washed with 50 mL of ether to remove excess CBZ chloride. The aqueous layer was acidified with 20 mL of 3N HCL and extracted with 4×50 mL of ethyl acetate. The combined extracts were dried over magnesium sulfate and the solvent was removed at reduced pressure to give a colorless syrup which started to crystallize. Recrystallization from chloroform gave 4.70 g (44% yield) of the desired product as white crystals (mp=94°–95° C).

$_1$H NMR (CDCl$_3$) 7.35 (s, 5H), 6.70 (s, 2H), 5.70 (s, 1H), 5.15 (s, 2H), 4.35–3.95 (m, 1H), 3.25–3.00 (m, 2H), 2.50 (d, 2H, J=6.5 Hz).

EXAMPLE XIV

1-N-Benzyloxycarbonyl-2,4-butanediol (12)

4.57 g (18.0 mmoles) of the acid (11) in 18 mL of dry THF was added dropwise with stirring to an ice cold solution of 1M borane-THF in THF (Aldrich Chemical Co.) under a blanket of argon. After the addition was complete, the mixture was stirred at room temperature for 30 min and then quenched with 36 mL of 10% acetic acid in methanol. The solvent was removed at reduced pressure and the residue was taken up in 80 mL of ethyl acetate and washed with 1.5N HCl water and sat. sodium bicarbonate. After drying over potassium carbonate, the solvent was removed at reduced pressure to give a white solid. Recrystallization from benzene/hexanes gave 1.69 g (39% yield) of the desired product as white crystals (mp=80.5°–82° C.).

$^1$H NMR (CDCl$_3$) 7.35 (s, 5H), 5.50 (t, 1H, J=6.0 Hz), 5.10 (s, 2H), 3.75 (t, 2H J=6.0), 4.10–2.65 (m, 5H), 1.60 (q, 2H, J=6.0 Hz).

EXAMPLE XV

1-Amino-2,4-butanediol (13)

1.69 g (7.06 mmoles) of the CBZ protected aminodiol (12) was combined with 800 mg of Pd(OH)$_2$ on carbon, 100 mL of ethanol and 20 mL of 1,4-cyclohexadiene and the mixture was refluxed for 16 h. TLC (10% methanol in methylene chloride) showed no remaining starting material. The mixture was filtered through Celite on a sintered glass funnel (ethanol wash) and the solvent removed at reduced pressure to give 0.84 g of the desired product as an amber syrup. Dilution to 7 mL with ethanol gave a 1M stock solution of the aminodiol (13).

1H NMR (D$_2$O) 4.80 (s, 4H), 3.80 (t, 2H, J=6.0 Hz), 4.00–3.65 (m, 1H), 3.40–2.50 (m, 2H), 1.95–1.55 (m, 2H).

EXAMPLE XVI

1-N-Cholesteryloxycarbonyl-2,4-butanediol (14)

To an ice cold solution of 6.0 mL (6.0 mmoles) of the aminodiol (13) in ethanol was added a solution of 2.25 g (5.00 mmoles) of cholesterol chloroformate in 5 mL of methylene chloride. The mixture was removed from the ice bath and stirred under argon for 1.5 h, then poured over 150 g ice water. The mixture was extracted with 2×150 mL ethyl acetate and the extracts were washed with 2×100 mL water, 1×100 mL brine, dried over magnesium sulfate and stripped of solvent. The solid residue was dissolved in 10 mL of THF and chromatographed through a 3.5×15 cm silica gel column (packed with 1:1/hexanes:ethyl acetate). After elution with 300 mL of 1:1/hexanes:ethyl acetate, 45:45:10/ hexanes:ethyl acetate: methanol was used to elute the product. Removal of solvent gave 2.04 g (79%) of sticky white solid.

$^1$H NMR (CDCl$_3$) 5.38 (d, 1H), 5.14 (t, 1H), 4.50 (m, 1H), 4.00–3.70 (m, 3H), 3.60–3.00 (m, 2 H), 2.40–2.20 (m, 2H), 2.10–0.60 (m, 3H).

EXAMPLE XVII

1-N-Cholesteryloxycarbonyl-2-hydroxy-4-dimethoxytrityloxy butane (15)

To a stirred solution of 1.74 g (3.35 mmoles) of the diol (14) in 25 mL of dry pyridine was added 1.36 g (4.02 mmoles) of dimethoxytrityl chloride, 0,655 mL of triethylamine, and 20.5 mg of 4-dimethylaminopyridine. The reaction mixture was stirred for 16 hr under argon, then partitioned between 25 mL of water and 75 mL of ether. The aqueous layer was extracted with another 75 mL of ether and the combined extracts were washed with water and brine, then dried over sodium sulfate and stripped of solvents. The residue was chromatographed through a 3.5×13 cm silica gel column (packed with 4:1/hexanes:ethyl acetate). The fractions containing product (contaminated with a yellow impurity) were combined and stripped of solvent giving 2.22 g of yellow solid foam. Repeated chromatography using 5% methanol in methylene chloride and 4:1/hexanes:ethyl acetate gave the pure product (15) as a pale yellow solid foam.

$^1$H NMR (CDCl$_3$) 7.45–7.10 (m, 9H), 6.80 (d, 4H, J=8.8 Hz), 5.38 (d, 1H), 5.05 (br t, 1H), 4.50 (m, 1H), 3.90–3.80 (m, 2H), 3.80 (s, 6H), 3.50–2.95 (m, 4H), 2.30 (m, 2H), 2.10–0.60 (m, 43H). Anal. Calcd for C$_{33}$H$_{73}$NO$_6$: C, 77.62; H, 8.97;N, 1.17. Found: C, 77.41; H, 8.97; N, 1.60.

EXAMPLE XVIII

1-N-Cholesteryloxycarbonyl-2-succinyloxy-4-dimethoxytrityloxy butane (16)

To a stirred solution of 415 mg (0.506 mmoles) of the alcohol (15) in 2 mL of dry pyridine was added 30 mg of 4-dimethylaminopyridine and 48 mg (0.48 mmoles) of succinic anhydride. The mixture was stirred under argon for 24 h. TLC (5% methanol in methylene chloride) indicated a trace of unreacted starting material. The mixture was stripped of solvent and residual pyridine was removed by co-evaporation with toluene (2×10 mL). The residual yellow solid foam was used for conversion to the p-nitrophenyl ester and immobilization to CPG.

EXAMPLE XIX

Cholesterol-CPG support (17)

The succinylated cholesterol derivative (16) was immobilized to long chain alkyl amine-controlled pore glass support (LCAA-CPG, Sigma) using the procedure of Atkinson and Smith (1984) in *Oligonucleotide Synthesis, a Practical Approach*, Gait, M. J. (ed.) IRL Press, pp 47–49. 105 mg of the crude succinate (16) was dissolved in 1.0 mL of dry dioxane along with 16 mg p-nitrophenol and 0.05 mL dry pyridine. Dicyclohexylcarbodiimide (52 mg, 0.25 mmoles) was added and the mixture was stirred for 15 min at room temperature and cooled in a refrigerator for 16 h. The crude p-nitrophenyl ester solution was filtered through a small pad of celite to remove DCU and the filtrate was added directly to 0.50 g of LCAA-CPG in 1.5 mL of DMF. 0.1 mL of ethyl diisopropylamine was added and the mixture was stirred for 18 h under argon. The CPG was filtered on a sintered glass funnel and washed with 3×10 mL of DMF, 3×10 mL of methanol and 3×10 mL of ether. The derivatized CPG was dried on a vacuum pump and "capped" by treatment with 1.5 mL of dry pyridine and 0.2 mL of acetic anhydride. After stirring for 3 h under argon, the CPG was filtered and washed with 3×10 mL of methanol and 3×10 mL of ether. Drying on a vacuum pump gave 0.46 g of cholesterol-CPG (17). The CPG was analyzed for DMTr content according to the protocol described in Gait and found to have a loading of 24 micromoles/gram of CPG support.

EXAMPLE XX

Synthesis of 3' cholesterol tailed 5' DMTr-thymidine from cholesterol-CPG (17)

To test the suitability of cholesterol-CPG (17) for oligonucleotide synthesis, a single thymidine residue was added to 41.6 mg (1 micromole) of the solid support. A Milligen DNA synthesizer was used along with standard phosphoramidite coupling chemistry. The 5'-dimethoxytrityl protecting group on the thymidine was not removed in order to aid in isolation and characterization of the product. The CPG was washed well with acetonitrile (8 mL) in order to eliminate trace amounts of unreacted DMTr-thymidine phosphoramidite and other non-covalently attached impurities. The CPG was dried on a vacuum pump and analyzed for DMTr content as described above and found to have a loading of 27 micromoles/gram. The 3'-cholesterol tailed thymidine was cleaved from 20 mg of the support by 24 h treatment with 10 mL of concentrated ammonia at 44° C. in a 5 mL Reactivial (Teflon liner). The 3'-cholesterol tailed thymidine was isolated by removing the supernatant (pasteur pipet) and washing the support with 3×2 mL of methanol. The combined washings were stripped of solvent (rotovap/vacuum pump) and analyzed by thin layer chromatography on silica gel plates using 7:1:1:1:1/ethyl acetate:acetone:methanol:water:acetic acid. One major DMTr containing spot (R$_f$ =0.63) stained orange upon spraying with 10% sulfuric acid in methanol. Only trace amounts of DMTr-thymidine (R$_f$=0.84) could be detected, thus indicating the stability of the cholesterol linkage. The CPG support after ammonia treatment for 24 h had a DMTr content of 1.4 micromoles/gram.

Ammonia treatment of DMTr-thymidine derivatized cholesterol-CPG for only 5 h at 44° C. gave TLC results which were similar to the 24 h treatment. The CPG support after 5 h of ammonia treatment had a DMTr content of 3.2 micromoles/gram.

The oligonucleotide from Example XII bearing an acridine 3'-tailed molecule thereon was studied as to its melting temperature characteristics in the presence of a complementary oligonucleotide strand. The presence of the acridine intercalating agent raised the Tm approximately 4° C. in comparison to a similar oligonucleotide that did not bear 3'-tailed acridine molecule.

Appropriate reporter groups attached to the 3' tail of appropriate oligonucleotides are useful for identifying the presence of the oligonucleotide. Fluorescence, chemiluminescence or other properties of such reporter groups serve to nonradioactively "tag" these nucleotides. The nucleotides can then be identified in a sample of interest, as for instance a biological sample, by the presence of fluorescence or other like property. A lipophilic tail group, as for instance, a cholesterol tailed 3' oligonucleotide, assists in the transfer of the oligonucleotide across the cell membrane. Thus increased concentration of the oligonucleotide within the cell or facilitated transfer of the oligonucleotide across the cell membrane is achieved. A cleaving group on the 3' tail of the oligonucleotide can assist in site specific cleavage of DNA bearing the oligonucleotide's complementary sequence after binding of the oligonucleotide to such complementary sequence. Such use might be implicated in gene identification, isolation and the like.

Other "tail molecules" or "conjugates" might be selected based on other properties both biological and physical. Such other biological tail molecules might includes appropriately blocked synthetic peptides, puromycin, digoxigenin and the like. Other tail molecules having useful physical properties might include spin-labeled compounds, DTPA chelating agents, phospholipids, di and trinitrolphenyl groups and cross-linking agents including alkylating agents, azidobenzenes, psoralen, idoacetamide, azidoproflavin and azidouracil.

While, for illustrative purposes, this invention has been described with reference to its preferred embodiments, other embodiments, variations and/or modifications might be evident to the art skilled given this disclosure. As such, limitation of this invention is not to the preferred embodiments, but is as is set forth in the following claims.

SCHEME I

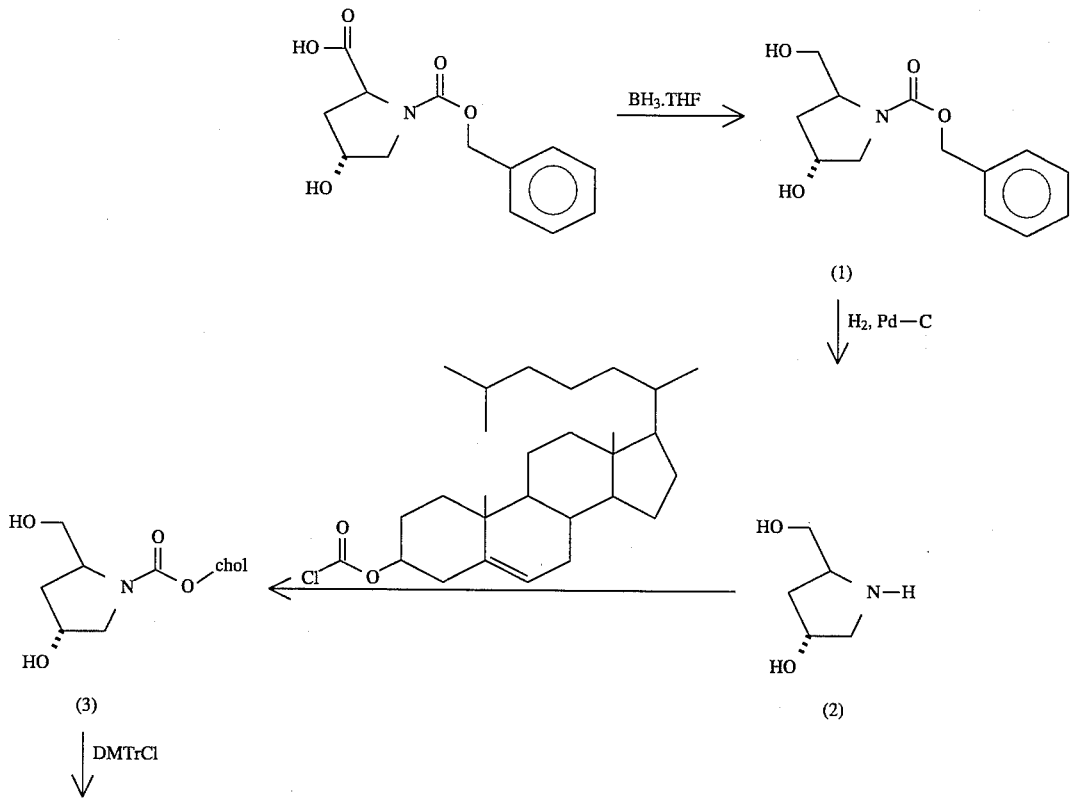

5,512,667
-continued
SCHEME I
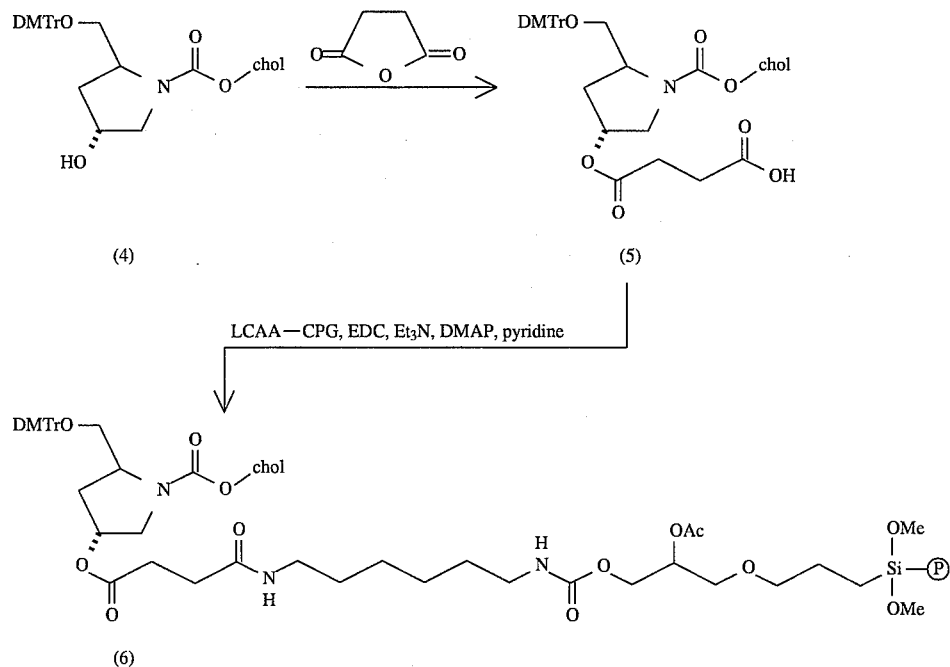
SCHEME II
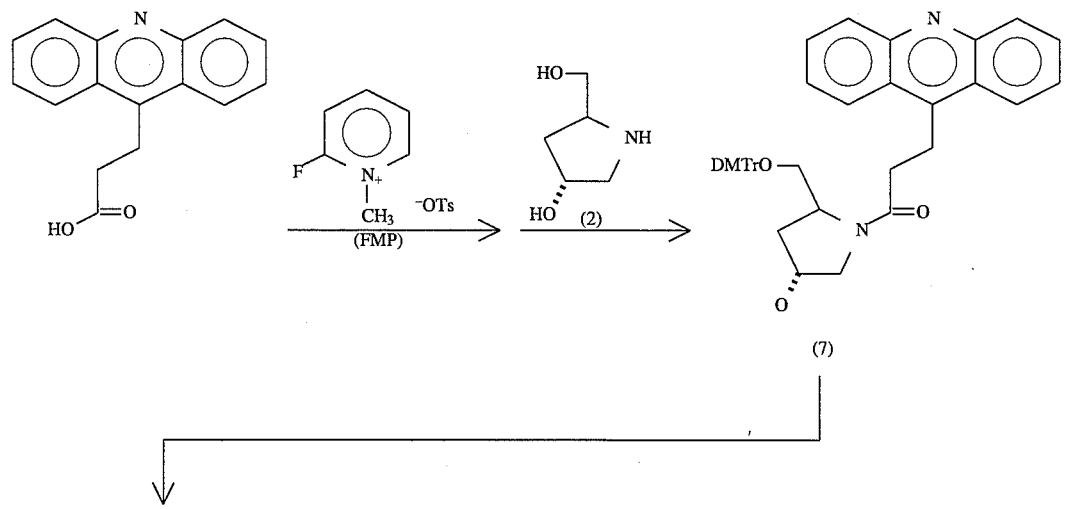

-continued
SCHEME II
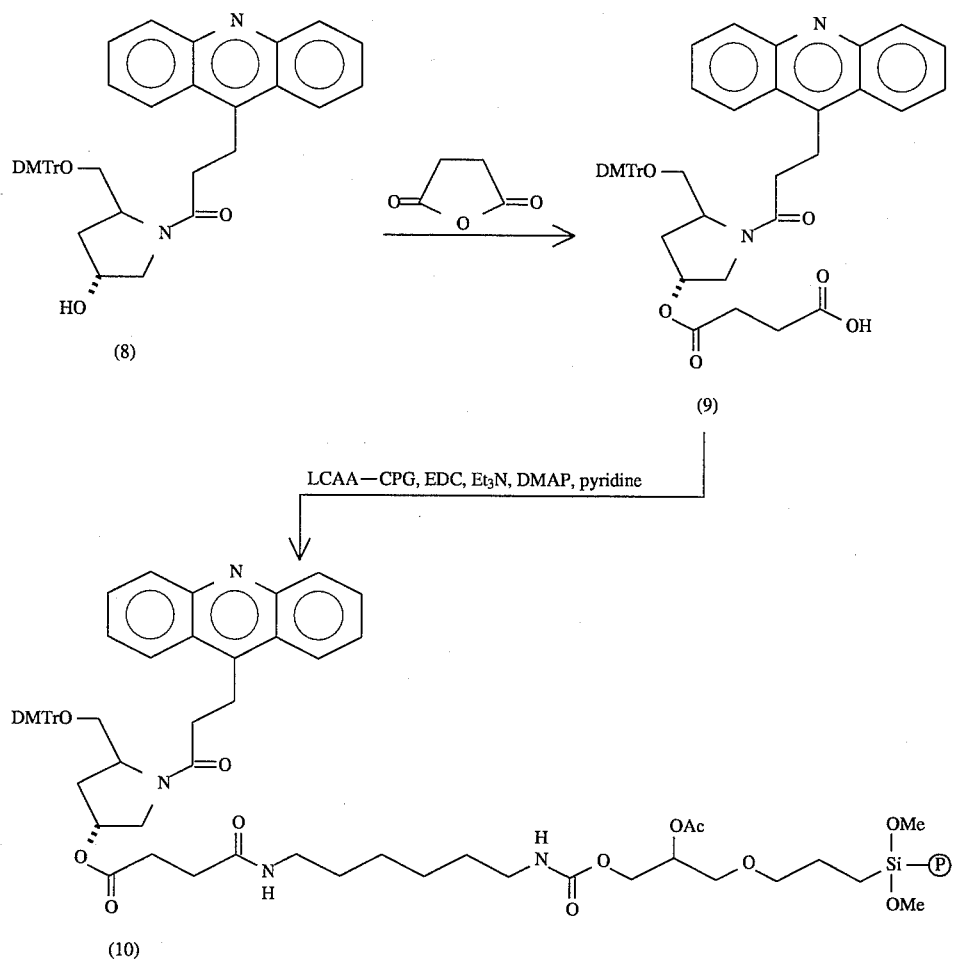
SCHEME III
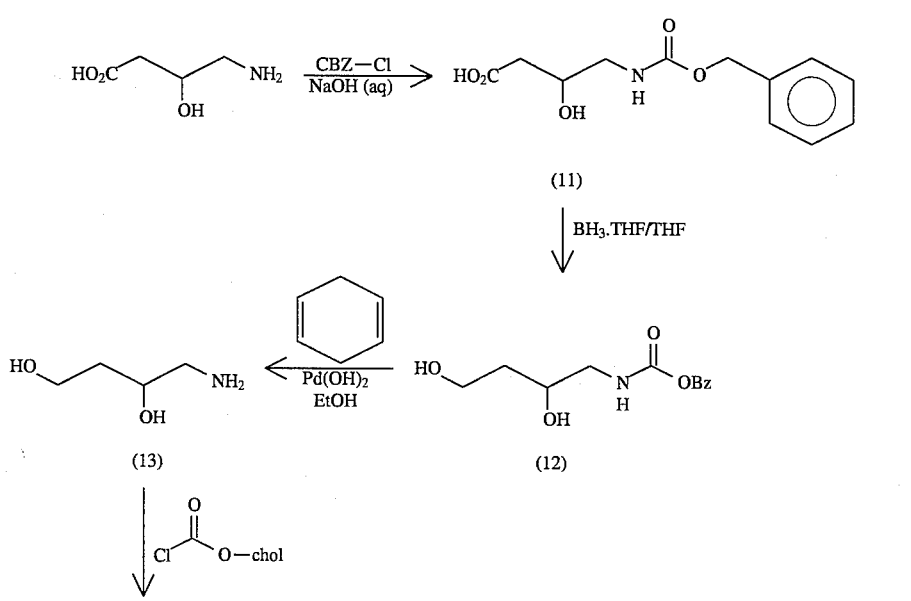

-continued
SCHEME III

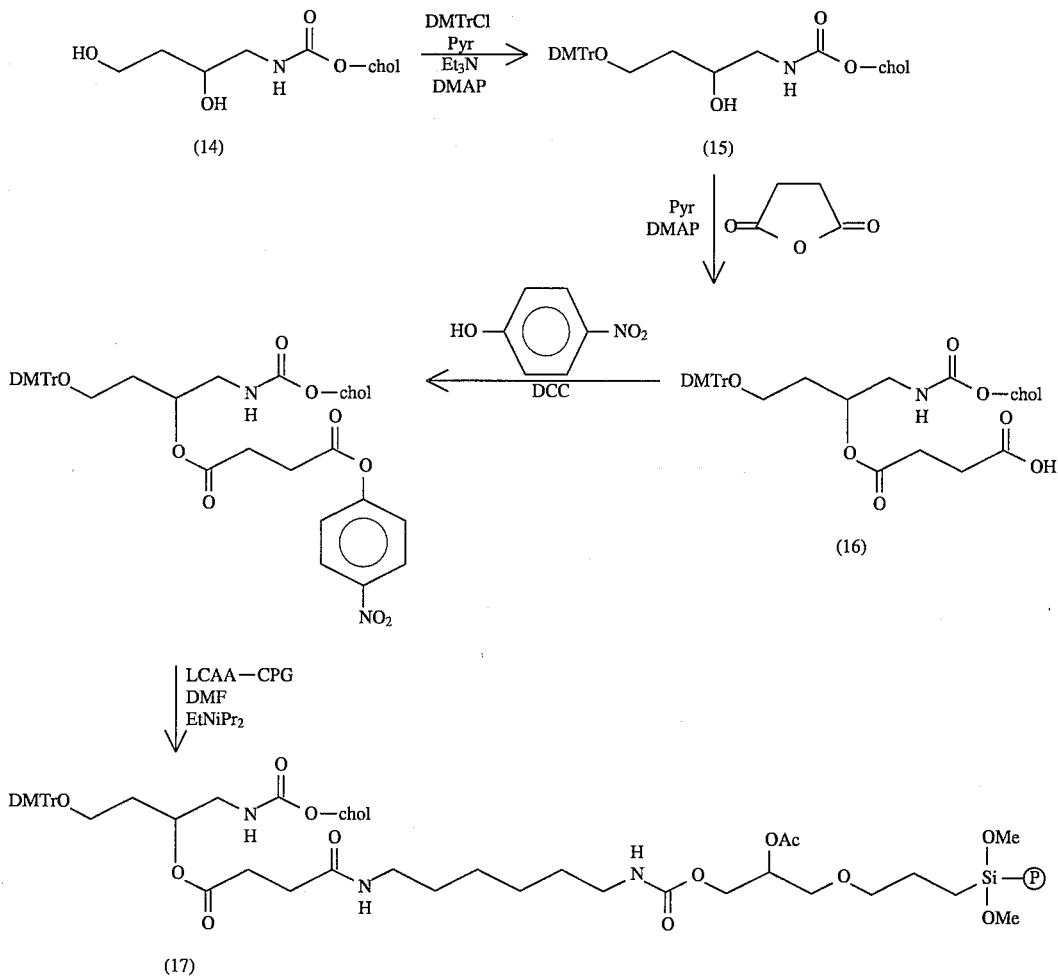

We claim:
1. A compound having the formula shown below:

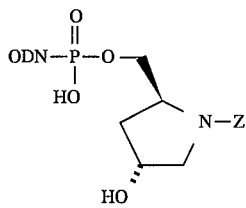

"wherein ODN represents an oligonucleotide whose terminal 3'-oxygen is attached to the above phosphate moiety" wherein Z is selected from a group consisting of

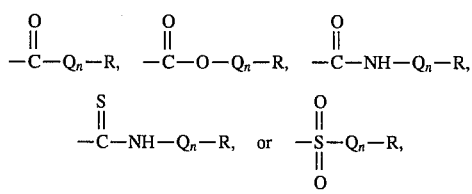

n is 0 or 1, Q is a connecting group selected from a group consisting of alkyl, alkoxy, alkoxyalkyl, alkenyl, cycloalkyl, aryl, aryloxy, aralkyl, heterocyclic, heteroaryl, substituted aryl and substituted aralkyl; and R is selected from the group consisting of intercalating groups, cleaving groups, cholesterol and lipophilic groups.

2. A compound of claim 1 wherein:

said R group is selected from a group consisting of cholesterol, acridine, ellipticine, methidium, ethidium, phenanthroline, 2-hydroxyethanethiolato-2,2', 2"-terpyridine-platinum(II), quinoxaline, an EDTA ligand for attaching Fe and a phenanthroline ligand for attaching Cu.

3. A compound of claim 1 wherein Z is

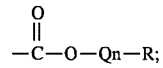

n is 0; and R is cholesterol.

4. A compound of claim 1 wherein Z is

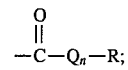

n is 0; and R is 9-acridine.

5. A compound having the structure:

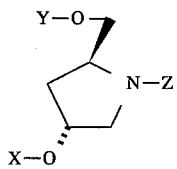

or

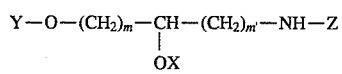

wherein

Z is selected from a group consisting of

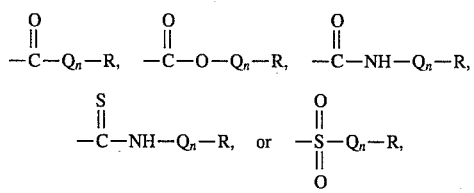

m and m' independently are positive integers less than 11; n is 0 or 1; Q is a connecting group selected from a group consisting of alkyl, alkoxy, alkoxyalkyl, alkenyl, cycloalkyl, aryl, aryloxy, aralkyl, heterocyclic, heteroaryl, substituted aryl and substituted aralkyl; R is selected from the group consisting of reporter groups, intercalating groups, cleaving groups, cholesterol and lipophilic groups; Y is H or dimethoxytrityl; and X is a solid phase support.

6. A compound of claim, 5 wherein R is selected from the group consisting of cholesterol, biotin, acridine, fluorescein, rhodamine, Lissamine rhodamine B, Malachite Green, erythrosin, tetramethylrhodamine, eosin, pyrene, anthracene, 4-dimethylaminonapthalene, 2-dimethylaminonaphthalene, 7-dimethylamino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarin, isoluminol, benzophenone, dansyl, dabsyl, mansyl, sulforhodamine, 4-acetamido-4-stilbene-2,2'-disulfonic acid disodium salt, 4-benzamido-4'-stilbene-2,2'-disulfonic acid disodium salt, ellipticine, methidium, ethydium, phenanthroline, 2-hydroxyethanethiolato-2,2', 2"-terpyridine-platinium-(II), quinoxaline, an EDTA ligand for attaching Fe and a phenanthroline ligand for attaching Cu.

7. A compound of claim 5 wherein X is a controlled pore glass support derivatized with an alkylamine.

8. A compound of claim 5 wherein Y is H.

9. A compound of claim 5 of the structure:

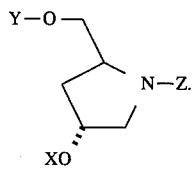

10. A compound of claim 9 wherein n is 1.

11. A compound of the structure:

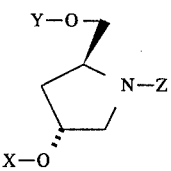

or

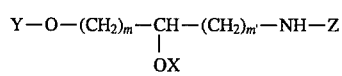

wherein

Z is selected from a group consisting of

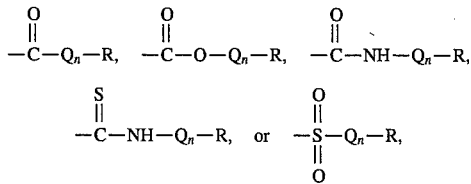

m and m' independently are positive integers less than 11; n is 0 or 1; Q is a connecting group selected from a group consisting of alkyl, alkoxy, alkoxyalkyl, alkenyl, cycloalkyl, aryl, aryloxy, aralkyl, heterocyclic, heteroaryl, substituted aryl and substituted aralkyl; R is selected from the group consisting of reporter groups, intercalating groups, cleaving groups, cholesterol and phospholipids; X is hydrogen, and Y is H or dimethoxytrityl.

12. A compound of claim 11 wherein R is selected from the group consisting of cholesterol, biotine, acridine, fluorescein, rhodamine, Lissamine rhodamine B, Malachite Green, erythrosin, tetramethylrhodamine, eosin, pyrene, anthracene, 4-dimethylaminonapthalene, 2-dimethylaminonaphthalene, 7-dimethylamino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarin, isoluminol, benzophenone, dansyl, dabsyl, mansyl, sulforhodamine, 4-acetamido-4-stilbene-2,2'-disulfonic acid disodium salt, 4-benzamido-4'-stilbene-2,2'-disulfonic acid disodium salt, ellipticine, methidium, ethydium, phenanthroline, 2-hydroxyethanethiolato-2,2', 2"-terpyridine-platinium-(II), quinoxaline, an EDTA ligand for attaching Fe and a phenanthroline ligand for attaching Cu.

13. A compound of claim 11 which has the structure:

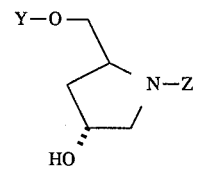

14. A compound of claim 13 wherein Y is H.

15. A compound of claim 13 wherein n is O; and R is cholesterol.

16. A compound of claim 13 wherein n is 1; Q is ethyl; and R is 9-acridine.

* * * * *

UNITED STATES PATENT AND TRADEMARK OFFICE
CERTIFICATE OF CORRECTION

PATENT NO. : 5,512,667
DATED : April 30, 1996
INVENTOR(S) : Reed et al.

It is certified that error appears in the above-identified patent and that said Letters Patent is hereby corrected as shown below:

Line 4,
Cover page, right column, in Abstract, move "Z is" after "wherein";

Column 5, line 61-62, "Z is wherein" should be --wherein Z is--;

Column 6, line 26, please delete "Z is";

Column 6, line 40, after "wherein" please add --Z is--;

Column 14, line 32, "(D2O)" should be --($D_2O$)--;

Column 17, line 25, "(0,184" should be --(0.184--;

Column 18, line 30, "$_1H$" should be --$^1H$--;

Column 19, line 19, "45:4510/hexanes-" should be --45:45:10/hexanes--;

Column 19, line 33, "0,655 mL" should be --0.655 mL--;

Column 27, line 53-54, please delete quotation marks;

Column 30, line 59, "n is O" should be --n is 0--.

Signed and Sealed this

Eighth Day of April, 1997

*Attest:*

BRUCE LEHMAN

*Attesting Officer*     Commissioner of Patents and Trademarks

UNITED STATES PATENT AND TRADEMARK OFFICE
CERTIFICATE OF CORRECTION

PATENT NO. : 5,512,667
DATED : April 30, 1996
INVENTOR(S) : Reed et al.

It is certified that error appears in the above-identified patent and that said Letters Patent is hereby corrected as shown below:

Column 1, line 9, before "BACKGROUND..." please insert the following paragraph --The U.S. Government has a nonexclusive, nontransferable, irreveocable paid-up license to practice or have practiced this invention for or on its behalf as provided for by the terms of Contranct DAMD 17-88-C-8201 awarded by the U.S. Department Army.--.

Signed and Sealed this

Sixteenth Day of June, 1998

*Attest:*

BRUCE LEHMAN

*Attesting Officer*  *Commissioner of Patents and Trademarks*